United States Patent [19]

Chang

[11] Patent Number: 5,100,777
[45] Date of Patent: * Mar. 31, 1992

[54] ANTIBODY MATRIX DEVICE AND METHOD FOR EVALUATING IMMUNE STATUS

[75] Inventor: Tse W. Chang, Houston, Tex.

[73] Assignee: Tanox Biosystems, Inc., Houston, Tex.

[*] Notice: The portion of the term of this patent subsequent to May 9, 2006 has been disclaimed.

[21] Appl. No.: 43,206

[22] Filed: Apr. 27, 1987

[51] Int. Cl.⁵ ............... G01N 33/543; G01N 33/545; G01N 33/552; G01N 33/577
[52] U.S. Cl. .................. 435/7.24; 422/57; 435/5; 436/510; 436/518; 436/519; 436/527; 436/531; 436/532; 436/548; 436/809; 436/811; 935/110
[58] Field of Search .............. 436/501, 518, 519, 531, 436/532, 527, 809, 815, 510, 548, 811; 435/7, 5, 7.24; 422/57; 935/110

[56] References Cited

U.S. PATENT DOCUMENTS

| | | | |
|---|---|---|---|
| 4,364,934 | 12/1982 | Kung et al. | 530/387 |
| 4,591,570 | 5/1986 | Chang | 436/531 |
| 4,677,061 | 6/1987 | Rose et al. | 435/39 |
| 4,829,010 | 5/1989 | Chang | 436/809 |

FOREIGN PATENT DOCUMENTS

| | | |
|---|---|---|
| 0063810 | 4/1982 | European Pat. Off. |
| WO84/03151 | 2/1984 | PCT Int'l Appl. |

OTHER PUBLICATIONS

In Patent Abstracts of Japan, vol. 8, Abstract #211 (p-303) 1984.

W. J. Herbert et al., Dictionary of Immunology, 3rd ed., Blackwell Scientific Publications, Oxford, U.K., 1985, pp. 136 and 153.

Primary Examiner—David Saunders
Attorney, Agent, or Firm—Eric P. Mirabel; Giulio A. De Conti

[57] ABSTRACT

An antibody matrix immunoassay device for determination of number and proportion of subpopulations of leukocytes is described. The device can be used to evaluate and monitor the immune status of an individual and to diagnose and monitor the progression of AIDS.

18 Claims, 1 Drawing Sheet

ANTIBODY MATRIX DEVICE AND METHOD FOR EVALUATING IMMUNE STATUS

BACKGROUND

Since Acquired Immune Deficiency Syndrome was first described in 1981, about 33,000 people have been identified as having AIDS and about 18,000 have died of the disease in the U.S. It has been estimated by the Center for Disease Control, U.S. Public Health Services, that in this country 1.5 million people have been exposed to the AIDS virus (Human Immunodeficiency Virus, HIV) and that by 1991, 5 million people will have been infected. Although there are groups identified as being at particularly high risk of developing the disease (e.g., homosexuals, intravenous drug users), increasing proportions of the infected people belong to groups not seen as high risk (e.g., heterosexuals, children, newborns). Recently, the World Health Organization warned that as many as 10 million people worldwide are infected with the AIDS virus and that in 10 years, as many as 100 million will be infected. It is not surprising that many health agencies around the world predict that AIDS will be the most common life threatening disease in the last part of this century and the beginning of the twenty first century.

When people are first infected with HIV, they develop antibodies against the virus. Most infected individuals remain symptom-free, although they continue to harbor the virus. Data have suggested that from 20-30% of those infected with HIV will develop AIDS and that of those who do, about 50% will die within 5 years. More recent studies have indicated that up to 75% will develop AIDS in 7 years. An even larger proportion of those infected will develop less severe immunodeficiency-related symptoms, referred to as AIDS-related complexes (ARC). Many patients with ARC eventually develop AIDS.

The AIDS virus is an unusual virus. It infects and destroys the CD4 antigen positive (CD4+) helper/inducer T cells, an important subpopulation of immunocytes involved in the regulation of immune responses. It has been shown that a very reliable indicator of the progression of infected individuals from symptom-free status, to ARC and then to clinical AIDS is a decrease in the number of CD4+ cells and the ratio of CD4+ to CD8+ cells. Thus, physicians generally prescribe assays to evaluate the immune status of individuals identified as seropositive or HIV-infected. Even individuals already determined to have ARC or AIDS are routinely monitored, by the lymphocyte subset determination, for disease staging purposes or for monitoring the results of therapeutic treatments.

Currently, the lymphocyte subsets are usually determined by fluorescence flow cytometric methods. This method requires costly equipment and specially-trained medical technicians. Although many major hospitals have set up facilities for carrying out these methods, most clinical laboratories, small hospitals, and doctors' offices find it difficult to do so. In economically underdeveloped countries, where AIDS is endemic, performing flow cytometry routinely is almost impossible because of the prohibitive expense and the technical capabilities necessary. A simpler, more easily conducted, less costly method of lymphocyte subset determination would be very valuable in the diagnosis and monitoring of AIDS, as well as other diseases.

SUMMARY OF THE INVENTION

This invention pertains to an immunoassay device and method for determining the numbers and relative proportions of leukocyte subpopulations in the blood of an individual for evaluation of the immune status of the individual. In general, the immunoassay device comprises a support which has a substantially planar surface on which is located an array of antibody-coated areas (spots) which serve as cell-specific immunoadsorbents for various types of leukocytes.

In one embodiment, six different types of antibody-coated spots (or sets of antibody-coated spots) are present on the surface of the support to provide a test device for determination of six different leukocyte populations in a sample of leukocytes. The cell populations are:
  a. all mononuclear leukocytes;
  b. all T lymphocytes;
  c. all B lymphocytes;
  d. helper/inducer T lymphocytes(CD4+, CD8- cells);
  e. suppressor/cytotoxic T lymphocytes (CD4-,CD8+ cells); and
  f. monocytes The array thus contains at least six different spots, each individually containing antibody against one of the cell types. Preferably the device contains sets of several antibody coated spots for each cell type. Each of the antibody-coated spots serves as a tiny, specific immunoadsorbent for one of the leukocyte populations. The spots are leukocyte type specific. Thus, for example, an antibody-coated spot containing antibody against the CD4 antigen (e.g. OKT4 antibody)—a distinctive phenotypic marker of helper T lymphocytes—adsorbs helper T cells specifically.

The antibody spots are normally of substantially uniform dimension (size and shape). Thus, from the number of cells adsorbed to a spot (of a known number of cells in a test sample), the number of each cell type in a test sample of leukocyte can be determined and consequently, the relative proportion of each cell type in the sample can be determined.

Antibodies which are reactive against the general population of mononuclear leukocytes can be antibodies specific for $\beta_2$ microglobulin or for HLA or B antigens, which are expressed by all cells. Antibodies against the surface antigen CD3, which is expressed distinctively by all T lymphocytes, can be used to test for these cells. B lymphocytes are immunoglobulin-producing cells and, thus, antibodies against immunoglobulin (preferably G and M) can be used to determine B lymphocytes. Antibodies against the CD4 and CD8 antigen can be used to specifically adsorb T helper and T suppressor subtypes, respectively. Finally, monocytes are identified with antibody against the OKM1 antigen or LeuM3 antigen.

In other embodiments of the device, different combinations of antibody-coated spots specific for the leukocyte subpopulations mentioned can be present on the surface of the support, thus providing devices useful for testing for certain subpopulations of leukocytes. For example, a device can consist of antibody-coated spots specific for all T lymphocytes and the two subpopulations CD4+ lymphocytes and CD8+ lymphocytes. Such a device could include, for example, spots coated with antibodies against the surface antigen CD3 (for all T cells), spots coated with antibodies against the CD4 antigen (for T helper/inducer subtype) and spots coated with antibodies against the CD8 antigen (for the T suppressor/cytotoxic T subtype). These spots make it possible to determine the number of all T lymphocytes, T helper cells and T suppressor cells, respectively and thus to determine the relative proportion of each cell type. Use of a device of this type would provide information about the T cell population of an individual.

The test devices of this invention make it possible to provide valuable information about the immune status of an individual. The immune defense against invading viruses and bacteria is mediated to a large extent by mononuclear leukocytes, which consist primarily of lymphocytes and monocytes distributed in the lymphoid system and blood circulation. The B and T lymphocytes generate both antibody and cell-mediated immune responses against the invading agents and these responses are, in turn, controlled by the helper and suppressor T lymphocytes.

The number of monocytes, B cells, T helper and suppressor cells and their relative proportions in the blood of normal, healthy individuals fall in defined ranges. In a given individual, the ranges are normally narrow. A change in these values in an individual usually indicates that the express or overall function of the immune system in the individual is undergoing a change. Thus, by monitoring the numbers and the relative proportions of subsets of the blood mononuclear cells, it is possible to determine whether the immune function of a person is normal, abnormal, deteriorating or improving.

Periodic assays of the immune status are highly desirable for individuals infected with HIV, the AIDS virus, and patients who have AIDS or ARC. HIV infects and destroys helper T cells and thus, lowers the ratio of helper T cells to suppressor T cells. In fact, the low number of T helper cells and the ratio of T helper to T suppressor cells has been used as the operational definition for clinical AIDS.

The assays carried out according to the method of this invention reveal the status of the immune system and thus provide information on disease state and progression. The nature and utility of these assays are distinctively different from current-available ELISA assays for measuring HIV antibodies. Currently availably ELISA assays merely detect past exposures to HIV or its antigens and do not measure the status of an individual's immune system and the clinical manifestation of the disease AIDS, as can be done using the method of this invention.

The immunoassay device may also be used to assess immune status in cancer patients and patients with autoimmune diseases and allergy. Patients under extensive treatments with chemotherapy or irradiation have damaged immune functions and are prone to infections, tumor metastasis, or secondary tumors. It is important to routinely monitor the immune status of these patients. Some severe cases of autoimmune diseases and allergies have abnormal proportions of leukocyte subsets with elevated levels of T helper cells. These proportions change from "baseline" or "normal ranges" during disease development. Such changes can be detected and monitored through use of the device and method of the present invention.

The above and other features of the invention including various novel details of construction in combinations of parts, will now be more particularly described with reference to the accompanying drawings and pointed out in the Claims. It will be understood that the particular immunoassay device embodying the invention, is shown by way of illustration only, and not as a limitation of the invention. The principles and features of this invention may be employed in varied and numerous embodiments without departing from the scope of the invention.

DETAILED DESCRIPTION OF THE INVENTION

Figure 1:
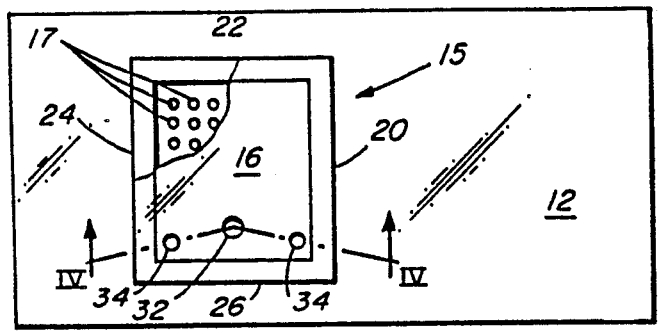
FIG. 1 is a plan view of an immunoassay device embodying the features of the present invention.

The immunoassay device of this invention comprises a support which has on its surface an array or matrix of antibody-coated spots specific for surface antigens expressed by mononuclear leukocytes and by various subpopulations of leukocytes.

The structural features of some embodiments of immunosay devices are generally described in U.S. Pat. No. 4,591,570, the teachings of which are incorporated by reference herein. Preferred structural embodiments of the device are described in U.S. patent application Ser. No. 025,501, by T. W. Chang, entitled "IMMUNOASSAY DEVICE WITH CHAMBERS ENCLOSING MATRIXES OF ANTIBODY SPOTS FOR CELL DETERMINATIONS", filed Mar. 13, 1987 (now U.S. Pat. No. 4,829,010), the teachings of which are also incorporated herein by reference.

In brief, the preferred device comprises a support surface such as a plastic or glass microscope slide, which has a substantially planar surface. On the support is the array of antibody-coated areas or spots specific for the various subtypes of leukocytes. The number of spots and the particular specificities depends on the type of test as described below. The spots are small, closely-spaced, discrete, antibody-coated areas of a predetermined, uniform dimension. The preferred arrangements of spots is a rectangular matrix. A cover is spaced from the support surface, positioned over the array (or matrix) of antibody-coated areas and secured to the support surface to provide an enclosed chamber. In the cover there is at least one aperture communicating with the interior of the chamber for introducing a liquid sample into the chamber. In addition, there is at least one additional aperture in the cover which also communicates with the interior of the chamber to allow air to escape upon introduction of sample into the chamber.

Preferably, the chamber is formed of a cover supported on four walls which are secured to the surface of the support and project upwardly therefrom. They form a rectangular enclosure located at the perimeter of the array of antibody coated areas.

The preparation of the antibody-coated areas is described generally in U.S. Pat. No. 4,591,570. The antibody-coated areas are normally small dots about 0.25 mm to about 2.0 in diameter. The dots are of uniform dimension and arranged as a compact matrix (e.g. 3×3, 4×4 or 5×5 matrices). The density of antibodies in the antibody-coated spots is related to the function of the spots as immunoadsorbents of cells. The density of coated antibodies (either covalently or non-covalently conjugated to the surface of the support) must be such that the cells bind tightly to the spots and remain bound during ordinary manipulation of the device in subsequent procedures for quantitating the bound cells. It is suspected that bridges between the surface antigens of the cells and the antibodies attached to the surface of the support must be sufficiently numerous in order to achieve tight cell binding. Preferably, however, the density of antibodies should be sufficient to yield, upon contact with an appropriate concentration of cells which have surface antigens that bind to the antibodies, a microscopically uniform layer of bound cells over the entire antibody-coated spot. The formation of such a uniform distribution of cells is desirable because this enhances the accuracy of quantitating cells bound to the spots.

Preferred antibodies for use in the device are monoclonal antibodies. Because the binding of protein to the support surface is dependent on its proportion in solution as well as its concentration, solutions of antibodies must be highly purified in order to obtain a sufficiently dense antibody coat for leukocyte adherence. Monoclonal antibodies against leukocyte surface antigens can be obtained in sufficiently pure solutions for preparing the antibody-coated spots. However, antigen-specific polyclonal antibodies can also be purified for the purpose of this invention.

Antibody spots of sufficient density for cell adherance can be obtained by applying solutions of antibody to the support surface having from about 10 ug/ml to about 20 ug/ml protein and being at least about 50% preferably greater than about 80% pure.

The surface containing the antibody matrix may be coated (except where the spot is located) with a visible, water repellant material such as tetrafluoroethylene or fluorinated ethylene-propylene to outline the antibody matrix.

The matrices of antibody-coated spots can consist of several different kinds of antibodies, which are selected on the basis of the type of test desired. In one embodiment, six different cell populations can be determined: mononuclear leukocytes, T cells, B cells, CD4+ cells, CD8+ cell and monocytes. The preferred antibodies for determining these cell types are:

| Cell Type | Antibody |
| --- | --- |
| Mononuclear leukocytes | anti-$\beta_2$ microglobulin |
| T cells | anti-CD3 |
| B cells | anti-immunoglobulin G and M |
| Helper/inducer T cells | anti-CD4 (OKT4 antibody) |
| Suppressor/cytotoxic T cells | anti-CD8 (OKT8 antibody) |
| Monocytes | anti-OKM1 |

The device contains six different types of antibody spots, each spot type containing one of the antibodies listed. Other devices can contain less than the six antibody types. For example, in another embodiment of this invention, which is particularly useful in assessing the status of an individual's T cell population—and thus in determining and monitoring the status of confirmed or suspected AIDS/ARC cases—the device includes antibody-coated spots specific for T lymphocytes, CD4+ lymphocytes and CD8+ lymphocytes. For example, such spots can be coated, respectively, with antibodies against the surface antigen CD3, antibodies against the CD4 antigen (OKT4 antibodies) and antibodies against the CD8 antigen (OKT8 antibodies).

Samples of an individual's mononuclear leukocytes can be obtained by any standard technique for isolating them from a sample of whole blood. A preferred method is to centrifuge anticoagulant treated whole blood through a dense medium (e.g. Ficol Hypaque ™ medium). Red cells and granulocytes will settle to the bottom of the tube and mononuclear leukocytes will be banded on top of the Ficol layer.

According to the method of the present invention, the leukocytes to be analyzed are placed in suspension in a suitable medium, such as phosphate buffered saline. The mononuclear leukocyte suspension is introduced into the sample chamber of the device and allowed to stand for sufficient time (about 20 minutes for a typical procedure) to allow the cells to settle on the test surface and for interaction to occur between the antibodies coated on the spots and cell surface antigens for which the antibodies are specific. Thereafter, non-adherent cells are removed by flushing the chamber with a wash solution, which can be normal saline or an aqueous buffer. If the cover is detachable, it can be removed and the test surface can be washed directly.

The matrix of the antibody-coated spots is subsequently examined to determine the numbers or quantity of cells bound to each spot. Quantitation of cells can be facilitated by fixing the antibody-coated spots after reaction with the sample. The binding of some or all cells to a particular spot indicates the antigen expressed by the cell and consequently the leukocyte type. The number of cells adsorbed to a spot gives the relative proportion of the particular cell type in the cell sample.

SPECIFIC CONSTRUCTION OF THE DEVICE

Figure 2:
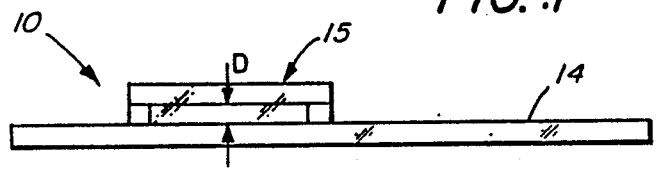
FIG. 2 is a side view thereof.
Figure 3:
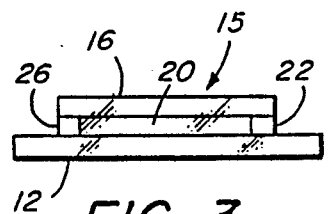
FIG. 3 is an end view thereof.
Figure 4:
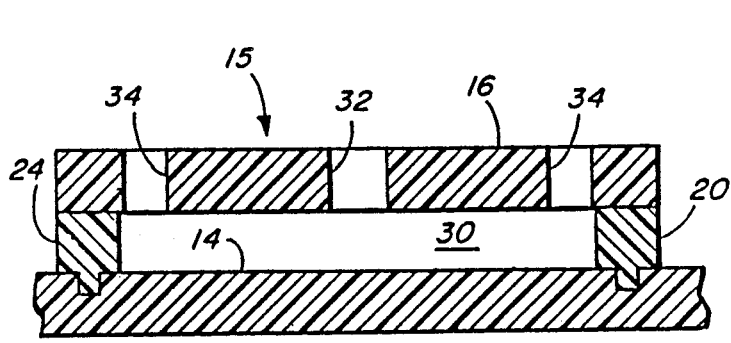
FIG. 4 is a sectional view of a portion of the device on an enlarged scale taken along the lines IV—IV on FIG. 1.

An immunoassay device shown in the drawings is generally designated 10. It includes a support 12, having a substantially planar surface 14. An array of small, closely-spaced discrete antibody coated areas 16 are located in an enclosed chamber 15 on the support surface and are shown only partially in FIG. 1. The enclosed chamber 15 comprises a cover 16 is spaced from the support surface by a distance D, as shown in FIG. 2, and is located over the array of antibody coated areas 17.

As shown in FIGS. 1 through 4, the cover is supported on four walls 20, 22, 24 and 26 which are secured to the surface 14 of the support surface 12, and project upwardly therefrom. As herein disclosed they form a rectangular enclosure located at the perimeter of the array of antibody coated areas 16, but it should be understood that other configurations may be employed without departing from the scope or spirit of the invention.

The cover 16, being mounted on the walls, extends a distance D above the surface 14 of the support 12 to create, together with the walls a chamber 30. The smaller the dimension D the quicker the cells will settle on the antibody matrix. For example, 0.3 to 2 mm have been found satisfactory.

The cover includes at least one aperture 32, which communicates with the chamber 30 for the introduction of the sample into the chamber and there is at least one other aperture 34 (there being two shown in FIGS. 1 and 4) to permit the escape of air when a sample is introduced into the chamber.

Figure 8:

As will be seen in FIG. 8, the cover and the walls may be integral, again creating a chamber 30 defined by the surface 14 of the support and the interior of a unitary member 36.

Figure 9:
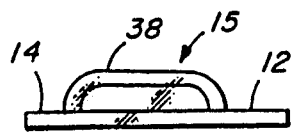
FIGS. 9 through 11 show other embodiments of the invention on a reduced scale.

The cover and walls may also be unitary being formed as a bubble or arcuate dome 38 as seen in FIG. 9.

Figure 10:
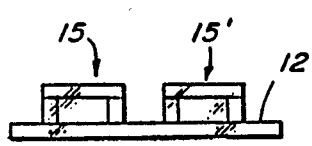

As seen in FIG. 10, there may be two or more enclosed chambers, 15 and 15' on one support, each one enclosing a matrix of antibody spots. This will allow samples of two different cell concentrations to be tested.

Figure 11:
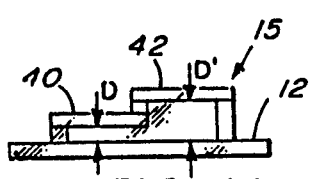

As seen in FIG. 11, the enclosed chamber 15 may also have two (or more) steps 40 and 42 of defined heights (distances D and D'). Thus, a single sample introduced into the chamber provides a different number of cells to matrices of antibody coated areas located under each step.

Figure 5:
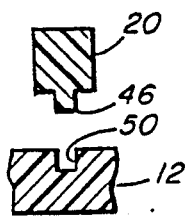
FIG. 5 is a detailed sectional view of one form of means for securing the walls to the support surface.
Figure 6:
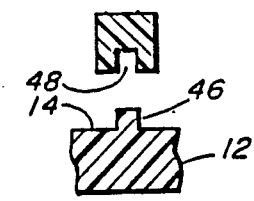
FIG. 6 is an alternative means of supporting and locating the walls.
Figure 7:
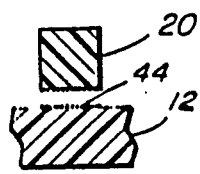
FIG. 7 is yet another alternative embodiment for the means for supporting the walls.

FIGS. 5 through 7 show various means of securing the walls to the support. FIG. 7 shows the wall 20 secured to the support 12 by adhesive material 44 either permanent or pressure sensitive which is compatible with the materials from which the immunoassay device is made.

FIG. 6 shows a dowel 46 projecting upwardly from the surface 14 of the support 12 which is engaged within a mating cylindrical opening 48 in the wall 20.

Conversely, the dowel 46 may be formed on the wall 20 and projected downwardly into a cylindrical opening 50 in the surface 14 of the support 12.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:
1. An immunoassay device comprising:
   a. support having a substantially planar surface;
   b. an array of small, closely-spaced, discrete, antibody-coated areas on the support surface, the array containing antibody coated areas each area individually containing one of the following antibodies:
      a. antibody specific for surface antigen present on all mononuclear leukocytes;
      b. antibody specific for surface antigen present on all B lymphocytes;
      c. antibody specific for surface antigens present on all T lymphocytes;
      d. antibody specific for surface antigen present on helper/inducer T lymphocytes;
      e. antibody specific for surface antigen present on suppressor/cytotoxic T lymphocytes; and
      f. antibody specific for surface antigen present on monocytes; and
   c. a cover spaced from the support surface and positioned over the array of antibody coated areas, the cover having at least one aperture communicating with the interior of the chamber for introducing a suspension of leukocytes into the chamber, and, at least one additional aperture in the cover also communicating with the interior of the chamber to allow air to escape upon introduction of the sample into the chamber.

2. An immunoassay device according to claim 1, wherein the antibodies in the antibody-coated areas are selected from the group consisting of:
   a. antibody specific for $\beta_2$ microglobulin;
   b. antibody specific for immunoglobulin G or M;
   c. antibody specific for surface antigen CD3;
   d. antibody specific for surface CD4;
   e. antibody specific for surface antigen CD8; and
   f. antibody specific for OKM1 antigen.

3. An immunoassay device of claim 1, wherein all of the antibody-coated areas are of substantially the same size and shape.

4. An immunoassay device according to claim 1, wherein the support is a glass microscope slide.

5. An immunoassay device according to claim 1, wherein the support is a plastic microscope slide.

6. An immunoassay device according to claim 1, wherein the array of discrete, antibody-coated areas is a rectangular matrix.

7. An immunoassay device of claim 1, wherein the antibody coated areas are formed by applying solutions of antibody to the support surface of from about 10 to about 20 ug/ml.

8. An immunoassay device of claim 1, wherein the cover is detachably secured to the surface of the support.

9. An immunoassay device of claim 1, wherein the cover is substantially rectangular and planar and is mounted upon walls which are secured to the surface of the support and extend upwardly therefrom.

10. An immunoassay device of claim 1, wherein the surface of the planar support is coated with a visible, inert, water repellant, material except where the antibody coated spots are located.

11. An immunoassay device of claim 10, wherein the coating material is tetrafluoroethylene or fluorinated ethylene-propylene.

12. An immunoassay device, comprising:
   a. a support having a substantially planar surface;
   b. a rectangular array of antibody-coated spots on the planar surface, the array of antibody-coated spots containing a spot or set of spots containing antibodies specific for $\beta_2$ microglobulin, a spot or set of spots containing antibody specific for immunoglobulin G, a spot or set of spots containing antibody specific for CD3 antigen, a spot or set of spots containing antibody specific for CD4 antigen, a spot or set of spots containing antibody specific for CD8 antigen, and a spot or set of spots containing antibody specific for OKM1 antigen;
   c. walls extending upwardly from the support surface and located at the perimeter of each array of antibody-coated spots; and
   d. a cover mounted upon the walls thereby forming an enclosed chamber over each array, the cover having a sample injection aperture communicating with the chamber space and a plurality of apertures also communicating with the chamber space to permit air to escape.

13. A device of claim 12, wherein the support and chamber are made of glass or plastic.

14. An immunoassay device of claim 12, wherein the array of antibody spots is comprised of three types of spots:
   a. antibody specific for surface antigen CD3;
   b. antibody specific for surface CD4; and
   c. antibody specific for surface antigen CD8.

15. A method of determining the numbers and relative proportions of leukocyte subpopulations in the blood of an individual, comprising:
   a. isolating leukocytes from the blood of an individual;
   b. introducing a sample of the isolated leukocytes into the chamber of an immunoassay device of claim 11, 12 or 14;
   c. allowing the leukocytes to settle onto the surface;
   d. removing nonadherent cells; and
   e. determining the number and proportion of leukocyte types by determining the number of leukocytes adhered to a type-specific spot.

16. An immunoassay device for monitoring the immune status of an individual infected with HIV, or diagnosed as having AIDS or ARC, comprising:
   (i) a support having a substantially planar surface;
   (ii) a rectangular array of antibody-coated spots on the planar surface, the array of antibody-coated spots containing antibodies specific for surface antigen present on leukocytes T lymphocytes, helper/inducer T lymphocytes and suppressor/cytotoxic T lymphocytes;
   (iii) walls extending upwardly from the support surface and located at the perimeter of each array of antibody-coated spots; and
   (iv) a cover mounted upon the walls, thereby forming an enclosed chamber over each array, the cover having a sample injection aperture communicating with the chamber and a plurality of apertures also communicating with the chamber to permit air to escape;
   wherein the support, walls and cover are made of glass or plastic.

17. An immunoassay device of claim 16, wherein the antibodies specific for antigens present on T lymphocytes, helper/inducer T lymphocytes and suppressor/cytotoxic T lymphocytes are anti-CD3 antibody, OTK4 antibody and OTK8 antibody, respectively.

18. A method of monitoring the immune status of an individual infected with HIV, or diagnosed as having AIDS or ARC, comprising the steps of:
   a. isolating leukocytes from the blood of the individual;
   b. introducing a sample of the isolated leukocytes into the enclosed chamber of an immunoassay device of claim 16;
   c. allowing the leukocytes to settle onto the planar surface of the chamber;
   d. removing nonadherent cells; and
   e. determining the number and proportion of leukocyte types by determining the number of leukocytes adhered to a type-specific spot.

* * * * *